US009827382B2

(12) United States Patent
Hausmann et al.

(10) Patent No.: US 9,827,382 B2
(45) Date of Patent: *Nov. 28, 2017

(54) FILTER SYSTEM FOR USE IN MEDICAL DEVICES

(71) Applicant: Boehringer Ingelheim International GmbH, Ingelheim am Rhein (DE)

(72) Inventors: Matthias Hausmann, Rees (DE); Steffen Schuy, Mainz (DE); Joachim Eicher, Ingelheim am Rhein (DE); Johannes Geser, Gerlingen (DE); Martin Meisenheimer, Appenheim (DE); Florian Witte, Schwabenheim (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/011,906

(22) Filed: Feb. 1, 2016

(65) Prior Publication Data

US 2016/0144138 A1 May 26, 2016

Related U.S. Application Data

(63) Continuation of application No. 13/809,897, filed as application No. PCT/EP2011/061288 on Jul. 5, 2011, now Pat. No. 9,283,333.

(30) Foreign Application Priority Data

Jul. 16, 2010 (EP) ..................................... 10169878
Jul. 16, 2010 (EP) ..................................... 10169883

(51) Int. Cl.
*A61M 11/02* (2006.01)
*A61M 11/06* (2006.01)
(Continued)

(52) U.S. Cl.
CPC ........... *A61M 11/003* (2014.02); *A61M 11/00* (2013.01); *A61M 11/007* (2014.02);
(Continued)

(58) Field of Classification Search
CPC ........ A01N 25/24; A01N 25/26; A01N 25/34; A01N 33/12; A01N 47/40; A01N 47/44;
(Continued)

(56) References Cited

U.S. PATENT DOCUMENTS 3,745,991 A * 7/1973 Gauthier et al. .............. 600/529
4,066,551 A * 1/1978 Stern ............................ 210/282
(Continued)

FOREIGN PATENT DOCUMENTS

DE 102007023012 A1 11/2008
EP 0521061 B1 12/1997
(Continued)

OTHER PUBLICATIONS

International Search Report and Written Opinion for PCT/EP2011/061288 dated Sep. 27, 2011.

*Primary Examiner* — Annette Dixon
(74) *Attorney, Agent, or Firm* — Marc Began; Philip I. Datlow

(57) ABSTRACT

A medical hand-held device, in particular an atomizer, for dispensing a liquid pharmaceutical preparation from a container with a discharge nozzle for the pharmaceutical preparation and located upstream from the discharge nozzle there is a multiple-stage filter system.

22 Claims, 7 Drawing Sheets

12e
12e
12d
12d
12
12a
12f
i
12c

(51) Int. Cl.

| | |
|---|---|
| ***A61M 11/00*** | (2006.01) |
| ***A61M 15/00*** | (2006.01) |
| *B05B 11/00* | (2006.01) |

(52) U.S. Cl.

CPC ............. *A61M 11/02* (2013.01); *A61M 11/06* (2013.01); *A61M 15/009* (2013.01); *B05B 11/3001* (2013.01); *B05B 11/308* (2013.01); *B05B 11/3091* (2013.01); *A61M 2205/7545* (2013.01); *A61M 2205/8281* (2013.01); *A61M 2207/00* (2013.01); *B05B 11/0043* (2013.01); *Y10T 29/49826* (2015.01)

(58) Field of Classification Search

CPC ... A01N 59/16; A61J 1/14; A61L 2/16; A61L 9/01; A61L 9/015; A61L 9/16; A61M 15/00; A61M 15/0086; A61M 16/00; A61M 16/009; B01D 17/04; B01D 17/045; B01D 39/00; B01D 39/16; B01D 39/1623; B01D 39/1692; B01D 39/20; B01D 39/2024; B01D 39/2027; B01D 46/0001; B01D 46/0004; B01D 46/0024; B01D 46/003; B01D 46/0031; B01D 46/24; B01D 46/2411; B01D 53/74; B01D 53/75; B01D 53/84; B01D 53/85; B01D 61/18; B01D 67/00; B01D 67/0069; B01D 67/0072; B01D 67/0079; B01D 67/0088; B01D 67/009; B01D 69/00; B01D 69/02; B01D 69/12; B01D 69/148; B01D 71/00; B01D 71/02; B01D 71/022; B05B 11/047; B65D 47/18; B82Y 30/00; C02F 1/44; C02F 1/444; C02F 9/00; C02F 9/005; D21J 7/00

USPC ............ 128/200.24, 203.12, 203.15, 205.27, 128/205.28, 205.29

See application file for complete search history.

(56) References Cited

U.S. PATENT DOCUMENTS

| | | | | |
|---|---|---|---|---|
| 5,490,938 | A * | 2/1996 | Sawan et al. | 210/651 |
| 5,497,944 | A | 3/1996 | Weston | |
| 5,869,073 | A * | 2/1999 | Sawan et al. | 424/406 |
| 6,837,866 | B1 | 1/2005 | Alexandre | |
| 6,988,496 | B1 | 1/2006 | Eicher | |
| 7,896,264 | B2 | 3/2011 | Eicher et al. | |
| 2004/0015126 | A1 | 1/2004 | Zierenberg et al. | |
| 2005/0129608 | A1 | 6/2005 | Takehara et al. | |
| 2011/0005517 | A1 | 1/2011 | Boeck et al. | |
| 2012/0174919 | A1 | 7/2012 | Hausmann et al. | |
| 2013/0199521 | A1 | 8/2013 | Hausmann et al. | |

FOREIGN PATENT DOCUMENTS

| | | | |
|---|---|---|---|
| EP | 0891712 | A1 | 1/1999 |
| EP | 2044967 | A1 | 4/2009 |
| EP | 2275160 | A1 | 1/2011 |
| JP | H0798134 | | 4/1994 |
| JP | 2008213022 | A | 9/2008 |
| WO | 9114468 | A1 | 10/1991 |
| WO | 9407607 | A1 | 4/1994 |
| WO | 9712687 | A1 | 4/1997 |
| WO | 9916530 | A1 | 4/1999 |
| WO | 0049988 | A2 | 8/2000 |
| WO | 2005000476 | A1 | 1/2005 |
| WO | 2009047173 | A2 | 4/2009 |
| WO | WO 2009047173 | A2 * | 4/2009 |
| WO | 2012007315 | A1 | 1/2012 |

* cited by examiner

FILTER SYSTEM FOR USE IN MEDICAL DEVICES

BACKGROUND OF THE INVENTION

The present invention relates to devices for administering liquid medicinal formulations in which the liquid is conveyed through narrow flow channels. In particular, the invention relates to small portable devices such as, for example, dosage dispensers, nebulizers or injectors as used for the measurement, inhalation or injection of liquid medicament formulations. In particular, the invention relates to a nebulizer for nebulizing ethanolic and/or aqueous medical formulations having a coarse filter for the depositing of particles which is inserted in a flow channel in front of a discharge nozzle.

From the prior art a multiplicity of medical devices and also specifically nebulizers are known which are operated with a liquid. In most of them the liquid is transferred into storage vessels or containers which contain a plurality of units to be administered by the device, with the result that the flow channels, metering units, delivery openings such as e.g. spray nozzles of the device, are used several times. In the field of nebulizers this applies for example both to propellant-containing metered dose inhalers (MDIs), in which on actuation of a metering valve the propellant gas expels the formulation from a storage container through the same nozzle over and over again, and to purely mechanical nebulizers such as, for example, standard commercial nasal spray systems or finger pump systems.

All these systems are potentially prone to the obstruction of flow channels or discharge nozzles. This obstruction may be caused, for example, by abraded particles during use or during the assembly of the system or by the agglomeration of formulation ingredients. The occurrence of this obstruction is dependent on the composition of the formulation, the solubilities of its ingredients, the interaction potential of the ingredients with one another and with components of the device in fluid contact and the behavior of the formulation under different climatic conditions, particularly at different temperatures.

EP 0 521 061 B1 discloses a metering device in the form of a purely mechanical nebulizer in which a measured amount of liquid medicament is conveyed into a pressurized chamber from which the liquid medicament is expelled through a nebulizer head by piston pressure. In the inlet channel of the nebulizer head there is a single filter—in the form of a lattice mesh, for example—for catching particles en route to the discharge nozzle.

A nebulizer with which liquid medicament formulations are nebulized for inhalation from a container holding several units of the formulation has been marketed by Boehringer Ingelheim KG for years under the name "RESPIMAT®". This purely mechanical miniaturized high pressure nebulizer is shown in WO97/12687A1 and WO09/047173A2. Using this nebulizer a liquid medicament formulation can be nebulized from a rigid container with an inner bag inserted in the nebulizer, as disclosed in WO00/49988A2, conveyed out of the inner bag by means of a piston pump driven by a helical thrust gear and, by means of a spring-operated pressure generator, nebulized in a pre-defined amount through a microstructured nozzle to form an aerosol intended for the lungs. The nebulization through the nozzle is based on the high speed impact of two microscopic jets of liquid, thus forming a fine mist. Details of possible microstructures for the discharge nozzle inserted in the nebulizers are disclosed in the specifications WO94/07607A1, WO99/16530A1 and WO05/000476A1. WO09/047173A2 describes the flow path of the medicament preparation from the container through a conveying tube into the pressure chamber and from there through a preliminary filter made of plastics into the microstructured discharge nozzle. According to the size exclusion principle, particles of the order of magnitude of the exit channels of the nozzle are trapped in the flow path before the nozzle.

In the specification U.S. Pat. No. 6,837,866B1 there is a description of the use of a filter in a needleless injection system. The active reagent is delivered by a jet of pressurized gas which, like a shock wave, breaks open the membranes between which the active reagent is located. The filter used here, comprising a stack of metallic nets, with a final ceramic layer, does not serve to filter the active reagent itself but purely to filter the pressurized gas and especially to cool it (when the jet of pressurized gas is generated, a pyrotechnic generator is used and the temperatures produced in the process should not come into direct contact with the active reagent).

The starting point for the development shown here is the filtering of liquids which has hitherto been integrated in medical hand-held devices such as the nebulizer described in WO09/047173A2.

The problem on which the present invention is based is to provide a device that is improved compared with the prior art, for administering liquid medical formulations—particularly a hand-held device such as a nebulizer or injector—which contains a filter system designed particularly for small flow cross-sections and designed for the depositing of all kinds of particles. The devices equipped with this filter system should be as independent as possible of their ultimate use, i.e. in particular independent of the choice of solvent in the formulation, the compatibility characteristics and the climatic conditions. The filter system and the associated assembly concept should be suitable for mass production.

In particular, the aim is to provide a filter system in which there is effective filtration of the liquid medical formulation. Particularly preferably, the filter system should filter out even the tiniest residues with a diameter of less than 1 μm from the inhalable solution, or abraded particles. Such tiny particles are not always picked up by typical size exclusion filters, which reliably filter out particles with a diameter at least in the micron range.

BRIEF SUMMARY OF THE INVENTION

The problem stated is solved according to the invention by a device for administering a liquid medical formulation which is held in a container inserted in the device and is expelled from the device through at least one, preferably two nozzle openings, wherein, before flowing through the at least one nozzle opening, the liquid medical formulation flows through a very fine filter, and inside the device, a pre-filter is arranged in front of the very fine filter, in the flow path of the liquid. The very fine filter and preferably also the at least one nozzle opening are formed by a microstructured component. The device is characterized in that inside the device, in the flow path of the liquid, a fine filter is additionally provided between the pre-filter and the microstructured component, the fine filter being different from the pre-filter, so that particles of different sizes or natures are deposited on the pre-filter and fine filter before the formulation enters the microstructured component.

Furthermore, the problem according to the invention is solved by a method of assembling a device which comprises a pressure chamber and filters arranged between the pressure chamber and nozzle channels, wherein the filters are introduced into a central part through what is to be the pressure chamber and the insertion opening is closed up by the piston of a pressure generator or by a connecting element, particularly configured as a hollow piston, for the subsequent withdrawal of liquid from a container.

Advantageous further features are described hereinafter and in detail by reference to the figures.

One feature of the present invention is that the filters have different pore sizes and are arranged so that the pore sizes become smaller in the direction of flow. The advantage of this invention is that in a system of this kind, comprising filters arranged behind one another, the particle deposition is distributed over a number of locations and in the event of a high particle load it does not result in total obstruction of the filter and hence of the device as a whole. This is particularly important for devices such as the hand-held devices preferably under consideration here, in which the liquid is passed through flow channels of restricted diameter even before being expelled through flow channels and wherein it is not possible to install filters of large surface area either because of the installation space available or because of fluidic conditions. In "tight" installation situations of this kind, the deposition capacity of an individual filter is limited because of its relatively small cross-sectional area.

A further feature of the present invention is that the filters are made from different materials. In this way, the filter effect determined by the pore size of the filters is supported by the different adsorption qualities of the filter materials: Depending on the material and surface nature of the filters, particles adhere to the filter in addition to being deposited by size. When different filter materials are used, different types of particles are also deposited by adsorption in this way.

A further feature of the present invention is that an adsorption filter is arranged in the flow path between the coarse filter and the discharge nozzle. The adsorption filter separates nanoparticles out of the liquid on the basis of intermolecular interactions such as, for example, electrostatic forces, van der Waals forces or the formation of hydrogen bridging bonds. The pre-filter, which is produced in particular from a plastics such as polyethylene, for example, and which may also be referred to here as a coarse filter, first of all precipitates particles down to an order of magnitude of about 9 μm in its flow path out of the liquid medical formulation, and the adsorption filter downstream thereof then filters nanoparticles, particularly up to a particle size of 5 nm, out of the liquid medical formulation. At high flow rates, nanoparticles of this kind cannot be filtered off by conventional size exclusion filters, on account of their small diameter. The depositing of the nanoparticles prevents such nanoparticles from accumulating at the outlets of the discharge nozzle and thus possibly adversely affecting the nebulization, or, particularly when two-jet nozzles are used, leading to a deviation in the direction of the jets of liquid. Preferably, an adsorption filter is used which, inter alia, guarantees a high throughflow rate. Particularly preferably, an adsorption filter with a large, particularly "inner" surface is used, so that as many nanoparticles as possible can accumulate thereon. Overall, the arrangement of the adsorption filter in the flow path increases the reliability of the nebulizer in terms of nebulizing the liquid medical formulation and effective filtration of the liquid medical formulation takes place to prevent adverse effects on the discharge nozzle.

A further feature of the present invention is that at least one filter consists of a preferably inert metal such as titanium, in particular. As a result, filter materials are obtained with good chemical compatibility particularly with formulations that are based on organic solvents such as ethanol, for example, and/or that have acid pH ranges, in particular. Preferably, the filter consists of sintered metal, as sintered structures can satisfactorily be pressed into structures with small cross-sections. A filter component made of sintered metal is mechanically stable and exhibits good installation properties, so that particularly when it is installed in a component of comparatively softer material or plastics no bypasses are formed at the side walls in the installed state. It has been found that by using sintered metal from splatter-fractionated metal powders it is possible to produce filters with particularly small pore sizes, so that smaller particles are filtered out than is the case with the particle filters used up till now in prior-art nebulizers.

Preferably, the fine filter is a filter of this kind made of metal, or an adsorption filter. Particularly preferably, the filter system comprises in addition to an adsorption filter a plurality of filters with which further particles are filtered out of the nebulized liquid medical formulation by the size exclusion method. In particular, the filter system comprises a coarse filter or pre-filter, a fine filter made of metal and an adsorption filter. The fine filter may be disposed, as desired, either between the pre-filter and the adsorption filter, or between the adsorption filter and the microstructured component that forms the nozzle or the very fine filter.

According to a further feature of the invention, the adsorption filter used here is made from glass, cellulose, carbon or polymer fibers and is subjected to functionalization of the surface before it is used. Thus, the carrier fiber is functionalized if, for example on account of its intrinsic surface properties, the carrier material cannot itself be used as an adsorptive fiber, such as for example a glass fiber (pH-dependent surface charges and free hydroxyl groups (OH groups) for the hydrogen bridge formation). One possible functionalization is carried out for example by means of quaternary ammonium groups, leading to the formation of surface charges. If the surface of the adsorption filter is positively charged in this way, typical negatively charged particles, preferably glass-like substances, may accumulate.

The possibility of functionalizing the surfaces of the adsorption filter using aluminium oxides is particularly preferred. This causes two different functionalities to form on the surface by means of which particles can be accumulated: both a positive charging of the surface and also hydroxyl groups of aluminium oxide hydroxide (AlO(OH)) on which particles can additionally accumulate by the formation of hydrogen bridging bonds. In experiments with the filters according to the invention, adsorption filters with a surface functionalized using aluminium oxide demonstrated good adsorption properties when using liquid medical formulations with pH values in the range from 3.5 to 9. When acid liquids are used, the protonation of the surface functionalized using aluminium oxide, and hence its positive charge, is reinforced, and in the case of basic liquids the formation of hydrogen bridges is intensified by an increased surface density of free OH groups.

In this way, when using adsorption filters functionalized using aluminium oxide, it is possible, in particular, to prevent the agglomeration of silica nanoparticles with a size of <<100 nm at the outlet from the discharge nozzle of the nebulizer. Silicates are fillers in typical elastomeric seals of the kind that are also used in nebulizers. Therefore, silica nanoparticles of this kind may be produced for example as abraded material during the use of the nebulizer, as has surprisingly been established. Known filters operating by the adsorption principle are obtainable on the market under different brand names; mention may be made of NANOCERAM®, from Argonide Advance Filtration Technologies, Sanford, Fla., USA, as a filter with an electropositive filter material, and alternatively ZETAPLUS®, from 3M Purification Inc., St. Paul, Minn., USA, or Disruptor™, from Ahlstrom Corporation, Helsinki, Finland. In addition, standard commercial glass fiber filters with a correspondingly large free surface area are useful as adsorption-based filters for dilute dispersions (e.g. glass fiber filters from GE Whatman GF Series). The filter materials mentioned above are merely examples, while other filter materials based on adsorption are not excluded from use.

By the term "filter capacity" is meant, in filtering using the size exclusion principle, a measurement of the quantity of particles that can be trapped by the filter as liquid passes through simultaneously. The filter threshold in this context is a measurement of the size of the particles that are retained by the filter. This filter threshold constitutes the degree of separation of the filtering, i.e. for the pore size specified for the filter threshold, there is a defined high probability, of e.g. 90%, that particles of at least this size will be deposited on the filter, according to the standards used.

The filter threshold of a filter is determined by its pore size. The pore size of a filter can be described by the computed size of the pore diameter, the distribution of which can be determined using the Washburn equation (E. W. Washburn, Proc. Natl. Acad. Sci. USA, 7, 115 (1921)) from measured data obtained by established capillary pressure measuring methods such as, in particular, mercury porosimetry, as described for example in German Standard DIN 66133.

The devices shown here for administering liquid medical formulations are preferably hand-held devices such as nebulizers or injectors with which defined volumes of liquids are delivered, i.e. nebulized or injected.

Besides pure liquids and solutions, the term "liquid" additionally encompasses dispersions, suspensions, solutions (mixtures of solutions and suspensions) or the like. The term "medical formulation" or "medicament formulation" according to the present invention, besides referring to formulations containing medicaments and active substances, also denotes therapeutic substances or the like, particularly every kind of agent for inhalation or administration by other means.

The individual features of the present invention may be used independently of one another or combined with one another.

BRIEF DESCRIPTION OF THE DRAWINGS

Further advantages, features, properties and aspects of the present invention will be apparent from the claims and the following description of preferred embodiments by reference to the drawings, wherein:

In the figures the same reference numerals are used for identical or similar components, where corresponding or comparable properties and advantages are obtained even if the associated description is omitted.

DETAILED DESCRIPTION OF THE INVENTION

Figure 1:
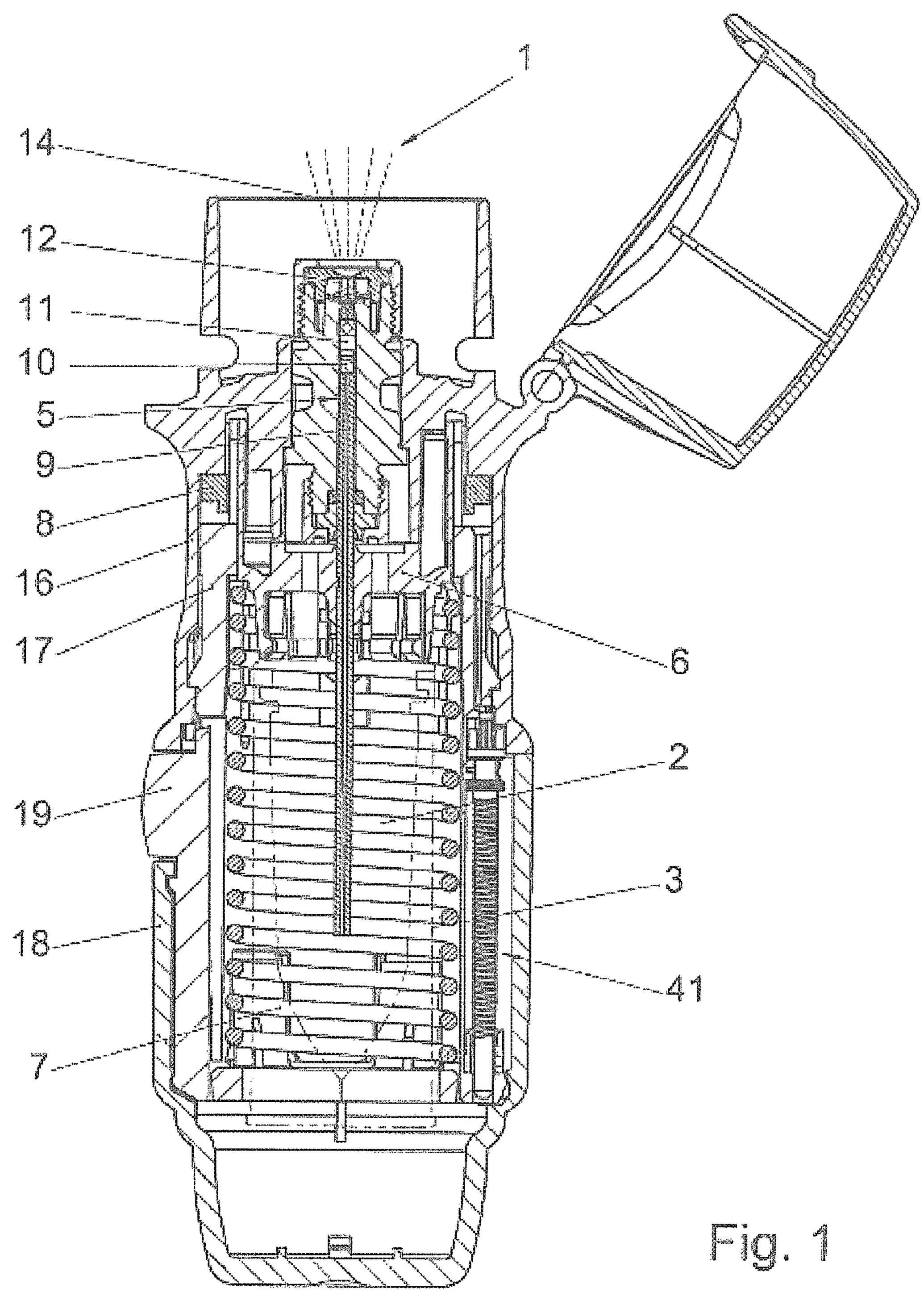
FIG. 1 is a schematic section through a nebulizer in the untensioned state.
Figure 2:
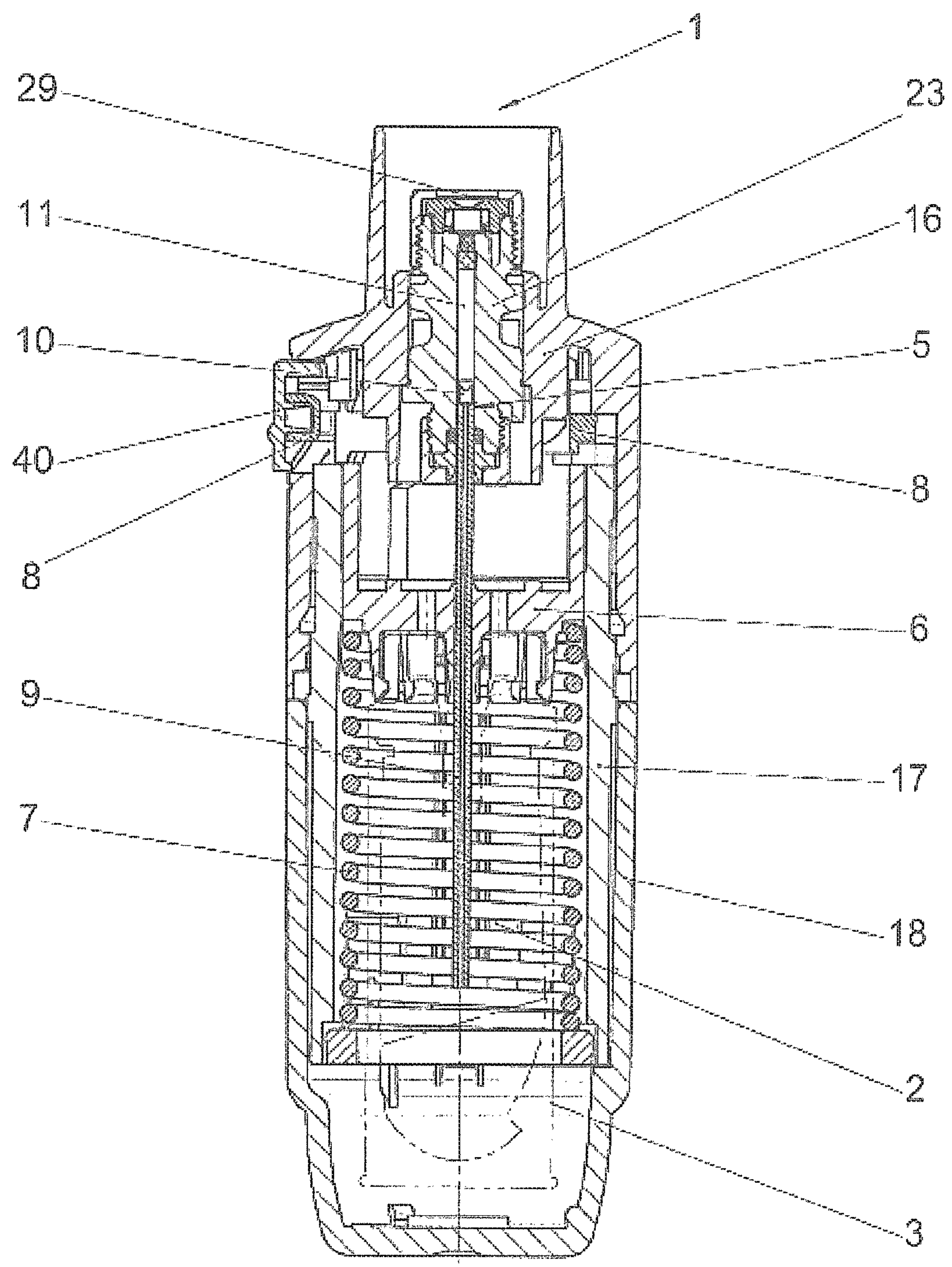
FIG. 2 is a schematic section through the nebulizer of FIG. 1, rotated through 90° compared with FIG. 1, in the tensioned state.

FIGS. 1 and 2 show, in schematic view, a manually operated medical device in which the proposed filter concept can be installed. The device shown in FIGS. 1 and 2 is a propellant-free nebulizer (1) which, on each actuating cycle, delivers the predetermined amount of a liquid (2) or a liquid medical formulation as a preferably lung-bound or inhalable aerosol (14). This aerosol (14) with droplets having aerodynamic diameters of preferably 0.5 to 10 microns, particularly 0.5 to 5 microns, can be breathed in by a user (not shown). A suitable nozzle is used for the nebulization, which is integrated in a microstructured component (12) in the embodiment shown. If the nozzle of this device used for nebulization is exchanged for the head of a liquid dispenser or an injection nozzle or a cannula or other injection device, all the operating principles independent of the nozzle remain unchanged, with the result that the correlations described hereinafter apply analogously to injectors or other liquid-delivery systems, even though only nebulizers are mentioned in the interests of simplicity.

In the operation of the nebulizer, a distinction is made between the untensioned state with an unfilled metering volume in the pressure chamber (11) (FIG. 1) and the tensioned state with the pressure chamber (11) filled (FIG. 2).

During the tensioning of the nebulizer (1), its upper housing part (16) is rotated relative to the inner housing part (17) and lower housing part (18) by a fixed rotation angle, e.g. 180°. A helical thrust gear mounted inside drives a piston pump by relative rotation, so that a predetermined, optionally adjustable amount of liquid (2) is conveyed from the container (3) into the pressure chamber and at the same time the drive spring (7) of the pressure generator (5) is tensioned (the final state of the tensioning process is shown in FIG. 2). When the nebulizer (1) is actuated, i.e. by the operation of a locking ring (8) using a button (40), the energy of the pressure generator (5) stored in the drive spring (7) is released: The hollow piston (9) previously used for delivering liquid now presses into the pressure chamber (11) with its non-return valve (10) closed, so that the quantity of liquid predetermined by the stroke action of the hollow piston (9) is expelled from there through the nozzle. The device is now in the released state again (FIG. 1).

In the embodiment shown, the hollow piston (9) is fixedly connected to a holder (6) for the container (3), belonging to the pressure generator (5), for example by being injection molded, adhered or snap-fitted thereon. The container (3) is fixed in the nebulizer (1) by means of the holder (6), particularly by a clamping or latching action, such that the hollow piston (9) projects into the fluid chamber of the container (3) and/or is fluidically connected to the liquid (2) in the container (3) and the liquid can be aspirated through the hollow piston. The container may be exchangeable as required. For this purpose, the device housing may be configured so that it can be opened up or partially removed (e.g. in the form of a cap-like lower housing part as disclosed in WO07/128381A1).

The container (3), which is inserted into the nebulizer (1) equipped with a dosage indicator or a counter (41), is designed for the withdrawal of a plurality of dosage units. For this reason it has to be designed so that the internal pressure remains substantially unchanged even when liquid is withdrawn, so that the same amount of liquid (2) is always withdrawn on aspiration. This can basically be achieved using both a container (3) with a rigid container wall, the internal pressure of which is kept constant by means of a vent, as described for example in WO06/136426A1, and also a container (3) with a flexible wall which moves at least partly into the interior of the container as liquid is withdrawn and thus keeps the internal pressure constant by reducing the internal volume. Containers (3) in which the flexible wall is formed by a bag which is substantially deformable, compressible and/or collapsible are preferred. Containers of this kind are described in various embodiments in the publications WO00/49988A2, WO01/076849A1, WO99/43571A1, WO09/115200A1 and WO09/103510A1. Particularly preferably, the container consists of a flexible, multi-layer foil bag closed off at the bottom, which is directly connected at the top to a flange, preferably made of plastics, forming a grip, a container cap welded thereto for attachment to the holder (6) of the nebulizer (1), an outer protective sleeve and a top seal (for details see WO99/43571A1 and WO09/115200A1).

Figure 3:
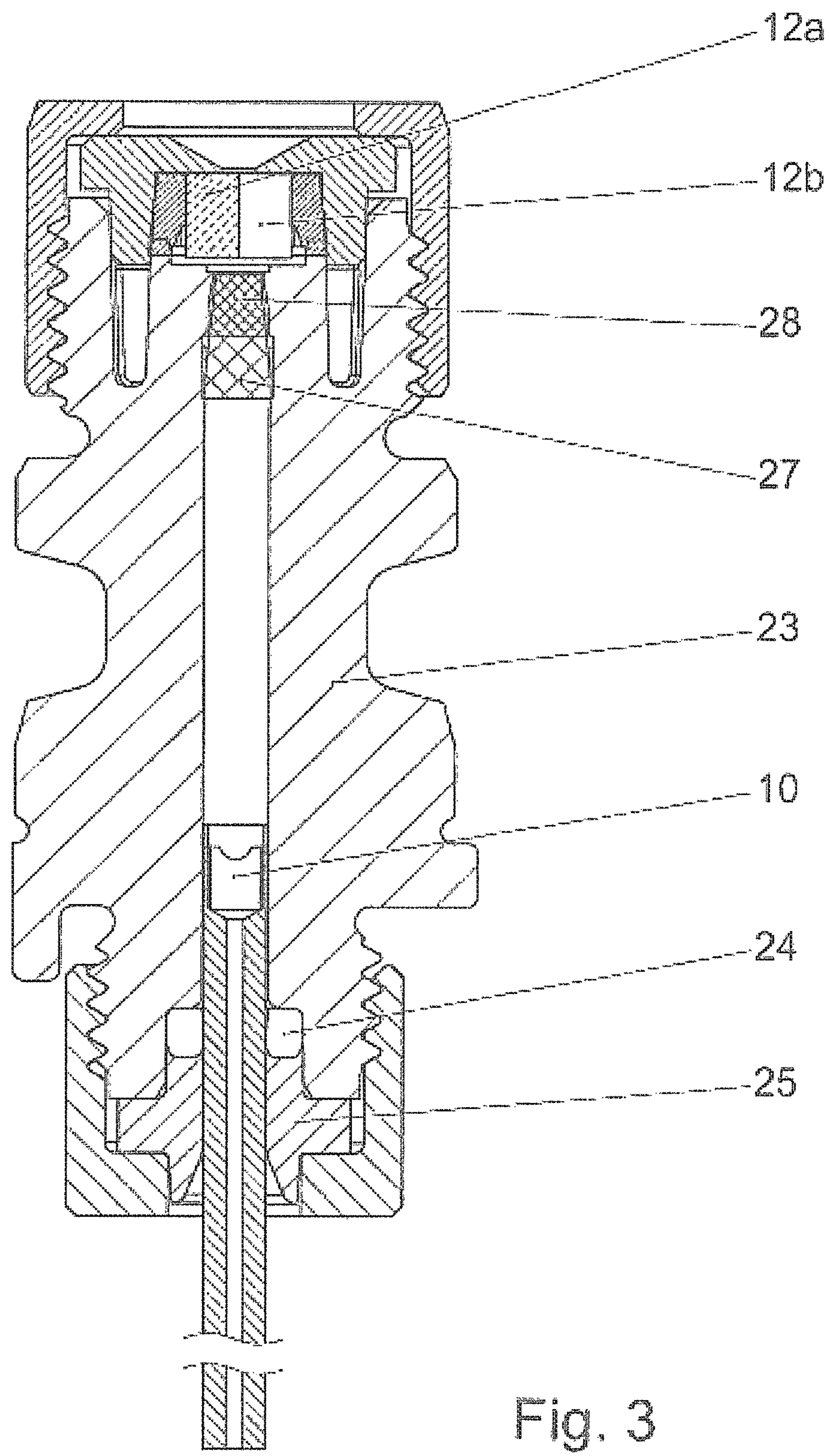
FIG. 3 is a schematic section through the nebulizer components of nozzle, filter mechanism, pump chamber and connecting element to the container.

FIG. 3 schematically shows the pressure chamber (11) of the nebulizer (1) which, in the embodiment shown, is suitable both for nebulizing aqueous liquid formulations and also, in particular, for nebulizing alcoholic liquid formulations. The hollow piston (9) belonging to the piston pump system projects into the pressure chamber (11) on the container side. The hollow piston (9) is also the connecting element between the pressure chamber (11) and the interior of the container (3). If the hollow piston (9) is partly withdrawn from the pressure chamber (11) during the tensioning process, a reduced pressure is produced by means of which liquid (2) is aspirated out of the container (3) into the pressure chamber (11) via the non-return valve (10) in the hollow piston (9), which is open in this situation. If the hollow piston (9) races into the pressure chamber (11) as the nebulizer (1) is actuated, the non-return valve (11) is closed by the abutment of its sealing surfaces on the seat in the hollow piston, and the liquid in the pressure chamber (11) is expelled under pressure through a filter system and the nozzle. The hollow piston (9) and pressure chamber (11) are sealed off by an elastomeric seal (24) which is, more particularly, in the form of an O-ring and is located in the guide tube of the piston close to its entry into the pressure chamber (11); the geometric position of installation of this seal (24), which is preferably compressed by means of a support ring (25), corresponds, for example, to that described in WO07/051536A1.

In the liquid outlet region of the pressure chamber (11) is a filter system which is located in front of the preferably microstructured component (12) into which the nozzle is integrated. The novel filter system shown here consists of a plurality of filter components arranged one behind the other, which differ in particular in the filter technology used. Preferably, the filter thresholds of the individual filter components are of such a size that each filter lets through smaller particles than the one before it, according to the principle of size exclusion. By the combination of different filter technologies and the arrangement of filters with a successively increasing separation level, or successively smaller pore sizes, a higher filter capacity is achieved overall, i.e. the deposition of larger quantities of particles without complete clogging of the filters, and a more thorough filtering. The first filter installed in the flow path with the largest pore diameter traps only the large particles, the next filter with a smaller pore diameter traps smaller particles, and so on. In this way, a fine-pored filter is not directly clogged by large particles to the point where it cannot allow any liquid at all to pass through.

In addition to trapping solid particles of a specific size, a filter may optionally catch additional material by adsorption. If filters of different types and different materials are used, this additional adsorption will vary from filter to filter. By the combination of different filter technologies, more particles and, in particular, particles that are deformable under pressure can also be trapped accordingly, thanks to the different adsorption effects.

The need for particle filtering arises in nebulizer technology in particular from the fact that the nebulizer nozzle has to be kept free from obstruction, to ensure its operational capability. In order to produce inhalable aerosols most nebulizer designs require very small nozzle structures which are often produced by so-called microsystem technologies such as lithographic manufacturing methods from semiconductor production or spark erosion or laser drilling techniques.

Figure 4:
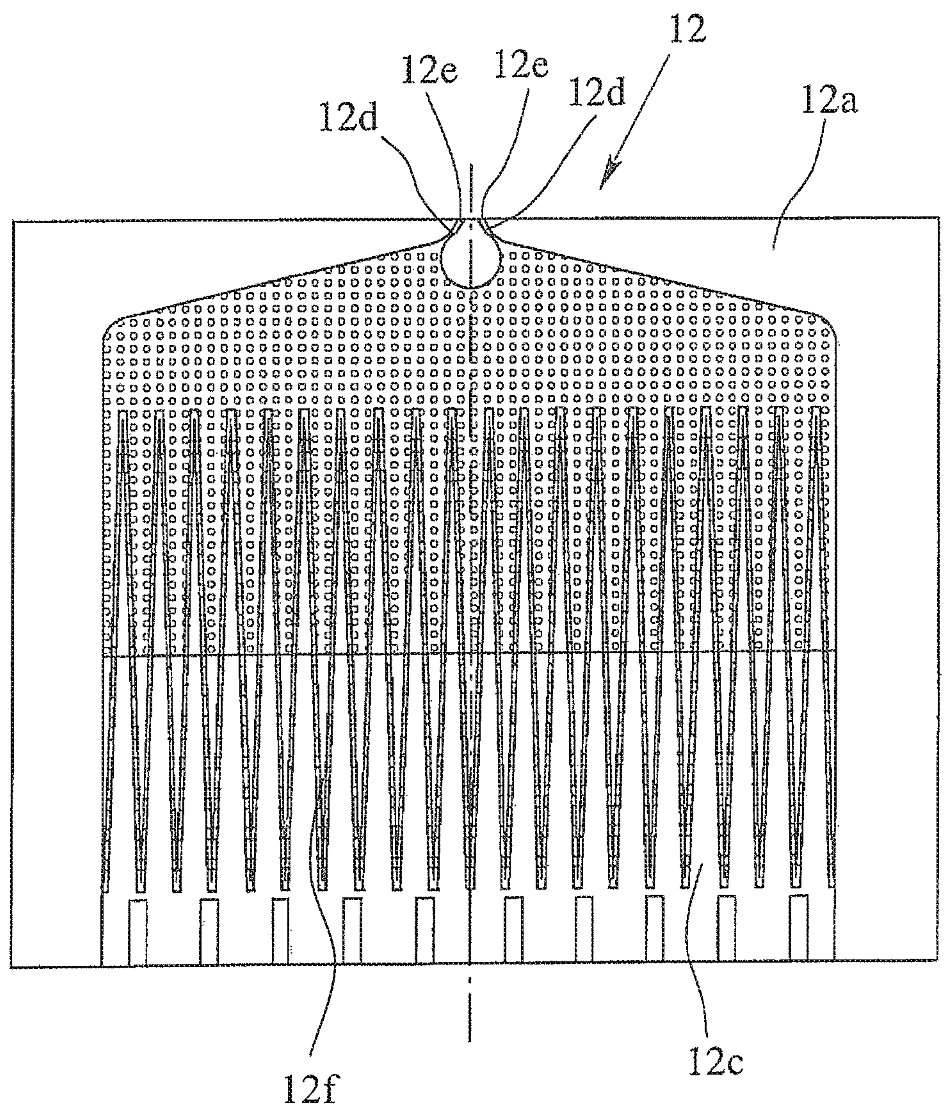
FIG. 4 is a section through a microstructured component or a schematic plan view of a part of the microstructured component for installation in a nebulizer, showing the microstructure with nozzle.

In the embodiment shown, the dimensions of the nozzle channels (12*d*) of the favored microstructured component (12) are just a few microns. Preferably, the nozzle channels (12*d*) have a rectangular profile with edge lengths of 2 to 10 microns. A microstructured component (12) that can be used for insertion in the specific embodiment is shown in FIG. 4. In the embodiment, the nebulization of the liquid with the nebulizer is preferably based on the high speed impact of two microscopic jets of liquid: liquid jets emerge from the preferably two nozzle channels (12*d*) or from the associated nozzle openings (12*e*), directed so as to meet at a defined angle, and are nebulized by the forces that act during the impact. If particles accumulate in these nozzle channels (12*d*) during the operation of the device, the liquid jets may optionally be diverted so that the impact and hence the nebulization is no longer complete or in extreme cases does not take place at all. For this reason, the particles have to be filtered out of the liquid (2) as completely as possible even before the liquid flows into the nozzle channels (12*d*).

Particles may be formed within the nebulizer in a variety of ways: by agglomeration or flocculation in the liquid medical formulation, by process steps during the assembly of the nebulizer and by abrasion caused by components moving against one another in the device, e.g. in the region of dynamic seals.

The central part (23) forms the lateral boundary of the pressure chamber (11), the liquid inlet in the form of the guide passage for the hollow piston (9) carrying the liquid, and the liquid outlet in which the filters are arranged in front of the nozzle. In the embodiment shown here, the pressure chamber is substantially circular-cylindrical. The construction of the nozzle and pump chamber system in the preferred embodiment is such that the central part (23) that defines the pump chamber comprises, at the hollow piston (9) end, a central bore—tapering preferably slightly conically in the downstream direction, i.e. progressively in the direction of throughflow—which both accommodates filter components, forms the pressure chamber (11) and receives the hollow piston (9) and, at a correspondingly wider point, the associated seal (24). Downstream, the nozzle assembly (29) which contains the microstructured component (12) that forms the nozzle and various associated holding or sealing components is attached to the central part (23).

Preferably, the filter component that is first after the pressure chamber (11) in the direction of flow is a coarse filter or pre-filter (27), which is directly followed by a fine filter (28). Further downstream there is the microstructured component (12) which forms the nozzle, and which contains not only the actual nozzle channels (12*d*) but also an integrated very fine filter (12*f*). In this way, the liquid flows in the device through three filtering components: a coarse filter or pre-filter (27), a fine filter (28) and finally a very fine filter (12*f*). Depending on the particle load or the freedom from particles required of the liquid that is delivered, it is also possible to incorporate additional filter elements. In a favored embodiment, the nozzle or the microstructured component (12), which comprises both the nozzle openings (12*e*) and also a very fine filter (12*f*), is made up of a microstructured plate (12*a*), preferably of silicon, and a plate (12*b*), preferably made of glass, that covers the structures. The structure thus incorporated, produced by microstructure techniques, first of all forms a very fine filter (12*f*) designed as a flow filter along the direction of flow behind an inflow region (12*c*) and then the nozzle channels (12*d*). The filter action is achieved by a special arrangement of solid struts and passages. Particularly preferred is a zigzag arrangement of rows of struts with very fine passages having a manufactured rectangular profile. The widths of the passages are just a few microns—preferably particles up to about 2 microns in size are removed from the liquid before it enters the nozzle channels and is later breathed in by a user of the inhaler after nebulization. Further details of possible structures for the microstructured component (12) or very fine filter (12*f*) installed in the nozzle assembly (29) are disclosed in the specifications WO94/07607A1, WO99/16530A1, WO05/000476A1, WO07/101557A2 and WO08/138936A2.

The complete system comprising the pressure generator (5) with drive spring (7), pre-filter (27), fine filter (28) and microstructured component (12) is preferably constructed so that during the production of the spray mist not only are droplet sizes formed that are adapted to pass into the lungs but the cloud of spray mist itself lasts long enough so that the patient can easily adapt their breathing to it. Spray times of 0.5 to 2 seconds, particularly 1 to 2 seconds, are preferred. The choice of the filter system and the filter thresholds in the nebulizer influences the length of the spray time. In particular, it has proved advantageous, in terms of the overall resulting spray time with the present filter system of pre-filter (27), fine filter (28) and very fine filter (12*f*), to use a fine filter (28) which causes a pressure drop of 30-70 bar in the present high pressure system and thus contributes to a prolongation of the spray time. The pressure drop is associated with the pore size of the filter: The smaller the filter threshold, for the same geometry, i.e. the smaller the pore size, the higher the pressure drop at the filter.

The filter components of the embodiment shown not only differ in terms of their filter threshold but are also varied in nature, structure and materials. The three filtering components of the device are a plastics filter, a metal filter and a microstructured component which is preferably made of a glass/silicon composite as described above. Thus, different materials are preferably used for the pre-filter (27) and for the fine filter (28) than for the very fine filter (12*f*). A pre-filter (27) made of plastics such as for example a polyolefin material that is chemically compatible with the majority of medical formulations, such as polyethylene (PE), polypropylene (PP) or polytetrafluoroethylene (PTFE), is particularly preferred. It is also possible to use a pre-filter (27) made of a modified polyolefin such as metallocene-PP, for example, while the special adsorption qualities of the material can be utilized. Preferably, the pre-filter (27) consists of compressed plastics granules or sintered material, in this case, most preferably, sintered polyethylene material. For the fine filter (28) it is preferable to use a metallic filter. In the embodiment shown here the fine filter (28) preferably consists of sintered metal, particularly in the form of metal particles of stainless steel or, most preferably, of titanium compressed into a fine-pored structure. In the flow path between a plastics filter with pore sizes 9 to 15 microns in diameter, for example, and a very fine filter (12*f*) with openings of 2 microns a fine filter with a comparatively average pore size in the range from 5 to 3 microns is preferred. Accordingly, the pore size of the metal filter is chosen to be sufficiently small for the pore diameter to be less than 5 microns. The multi-stage filter system shown here with a 2 micron opening width on the very fine filter (12*f*) is configured so that even very large active substance molecules or suspension ingredients are able to follow the flow path and be inhaled by the user by nebulization. Alternatively, it is also possible to use fine filters (28) or very fine filters (12*f*) as so-called sterile filters with pore sizes of as little as 0.05 microns or in the pore size range from 0.2 to 0.3 microns, as is preferred for sterile applications in the publication WO08/138936A2. The flow path and pressure generator then each have to be adapted to the higher pressure losses that occur at sterile filters. It has been found that filters with suitable pore sizes of less than 5 microns can be produced by sintering processes from metal powders of the kind that consist of so-called splattered particles clumped together at the surface. By using a splattered fractionated metal powder of this kind it is possible to produce particularly small pore sizes, so that it is possible to produce a metal filter with the particularly preferred pore diameter of 4 microns. It is particularly preferred to use titanium as the splattered fractionated metal powder, i.e. to use sintered titanium metal as a filter material. The use of baser metals can lead to the rapid formation of corrosion, particularly on account of the large surface area of a filter, particularly when there are components made of high-grade noble metals present in the same fluidic system, such as for example the preferred hollow piston (9) in the nebulizer in the embodiment shown by way of example. The use of a noble metal such as titanium, gold or platinum as a fine filter (28) in a medical system operated with liquid—the use of titanium being the most cost-effective option—also has the advantage that it is inert and thus chemically compatible with most medical active substances and formulation substances. In this way, the filter does not change the formulation, nor can it be changed, particularly corroded, by it. The latter is particularly important when using acid medical formulations, as preferred, in the pH range from 3.5 to 9 and particularly from 3.5 to 6, which may in turn lead to the corrosion of base filter metals. The filter system envisaged here is adapted to the filtering of acidic formulations of this kind.

Figure 5:
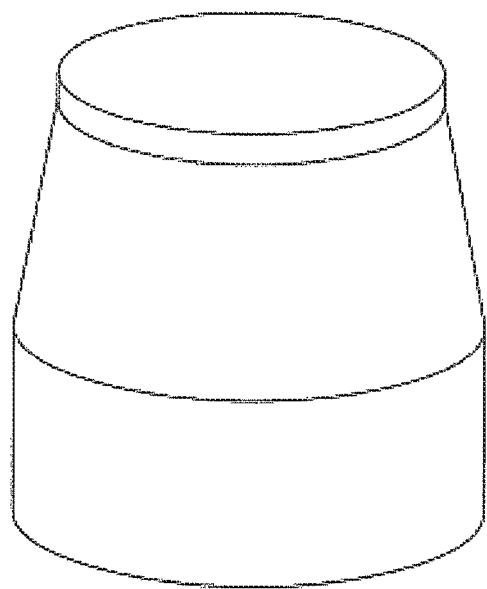
FIG. 5 is the side view of an individual filter element, tilted to the side, for installation in a medical hand-held device.

The special choice of the filter materials and the filter characteristics is, in the last analysis, dependent on the special intended application or the choice of the liquid (2) or medical formulation that is to be used and its compatibilities with other materials. The materials and installation concepts mentioned here already cover a broad range of requirements. In particular, devices with a filter system of this kind are suitable for administering a liquid medical formulation which contains a substance with a low vapor pressure or an alcoholic compound, e.g. as solvent. In the embodiment shown, the device comprises a central part (23) in which the two filters or the pre-filter (27) and the fine filter (28) are arranged downstream of a pressure chamber (11) or metering chamber which is formed by the same central part (23). The filters are thus arranged between the pressure chamber (11) and nozzle channels (12*d*). Both fine filter (28) and also pre-filter (27) or coarse filter have a circular-cylindrical or at least partly conical configuration. Particularly preferably, at least one filter has a shape with conically converging side walls that differs slightly from the circular-cylindrical shape. FIG. 5 shows a particularly preferred geometry of the fine filter (28). According to this, the fine filter (28) comprises, on the liquid inlet side, a circular-cylindrical structure which extends over a third to a half of the overall length of the fine filter (28) in the form of a constant circular diameter. Adjoining this circular-cylindrical area of the fine filter (28) is a conical region, so that the circular diameter of the fine filter (28) becomes smaller along the path of flow. At the flow outlet of the fine filter (28), the latter again has a narrow circular-cylindrical region. This combination of cylindrical and conically convergent regions of the side walls provides ease of assembly and at the same time good sealing of the fine filter with the inner wall of the central part (23) even when using metallic materials.

According to another embodiment which is not illustrated by the figures in this case, the pre-filter (27) and/or fine filter (28) may also be cup-shaped. A cup-shaped filter of this kind is installed in the device such that the opened side of the cup structure faces towards the pressure chamber. The upstream-facing cup structure of the pre-filter (27) and/or fine filter (28) has an entry surface which is significantly enlarged compared with the circular-cylindrical filter type, on which more particles can be deposited as they reach the filter. This is significant particularly for systems in which the formation of numerous, particularly large particles is of importance, as the filter capacity for these can be increased in this way.

According to yet another embodiment not shown here, the pre-filter (27) can be combined with the fine filter (28) in the form of a component with a graduated filter effect. In the case of the materials that are preferred here, the filter segments are sintered together. In the embodiment shown, the two filters have dimensions of less than five and particularly between 1 and 2 millimeters, so that they can easily be installed in miniaturized fluid systems such as the miniaturized high pressure nebulizer. During the assembly of the nebulizer (1), the filters are inserted one after the other into the appropriate central bore in the central part (23) and form, at the end of the pressure chamber (11), a press-fit with the inner wall of the central part (23). The pre-filter (27) and fine filter (28) are thus held in the central part (23) without any further components to secure them. In addition to or instead of the press-fit and/or frictionally locking connection, the central part (23) may also hold the filters by a reduction in its internal cross-section, so that the filters in the direction of flow are fixed, particularly in the direction of flow. The choice of materials for the filters is also of significance to the situation in which they are installed: particularly preferably, a filter made of metal, in this case the fine filter (28), follows the filter made of comparatively soft plastics, in this case the pre-filter (27), in the flow path. Particularly when used in a high pressure system this has the advantage that the metal filter can assume a retaining function for the plastic filter. Depending on the geometric design of the manufactured guide passages in the central part a soft plastic filter could be deformed, possibly damaged or forced out of its tightly fitting position under a high fluid pressure. This is prevented by its being held in place by the comparatively dimensionally stable metallic filter.

The choice of a hard metal such as titanium as a material for the fine filter (28) when installed in a central part (23) made of plastics has the advantage that, during conical compression, the solid metallic fine filter (28) presses into a superficially softer plastics material of the central part (23) such that no bypasses can be formed at its sides. In the preferred assembly process, in which the fine filter (28) is inserted in front of the pre-filter (27) into the same guide passage on the central part (23), it is advantageous that the central part (23) is superficially softer than the fine filter (28) but superficially harder than the pre-filter (27). If the pre-filter (27) consists of a particularly superficially soft material such as PE or PP, for example, a particularly tight fit is achieved relative to the side wall when it is compressed in the harder central part, so that once again the formation of bypasses is prevented. Particularly preferably, the central part (23) consists of a solid, pressure-resistant plastics such as PEEK, for example.

Looking at the assembly process for the device as a whole, the filters are inserted into the central part (23) through what is to be the pressure chamber (11) and the insertion opening is subsequently closed off by the piston of the pressure generator (5) or by a connecting element configured in particular as a hollow piston (9) for the later withdrawal of liquid (2) from a container (3).

In another embodiment (not illustrated here), the fine filter (28) may be a metal mesh filter, the fine-pored structure of which is produced by superimposing a number of layers of fine-mesh nets. These nets may for example be molded on directly in the central part (23) during the injection molding process. Alternatively, the mesh is embedded as a separate self-contained filter element in a plastic such as TPE or, most preferably, an elastomer, so that a single component contains not only the filter but also its associated retaining element or, preferably, sealing element.

Figure 6:
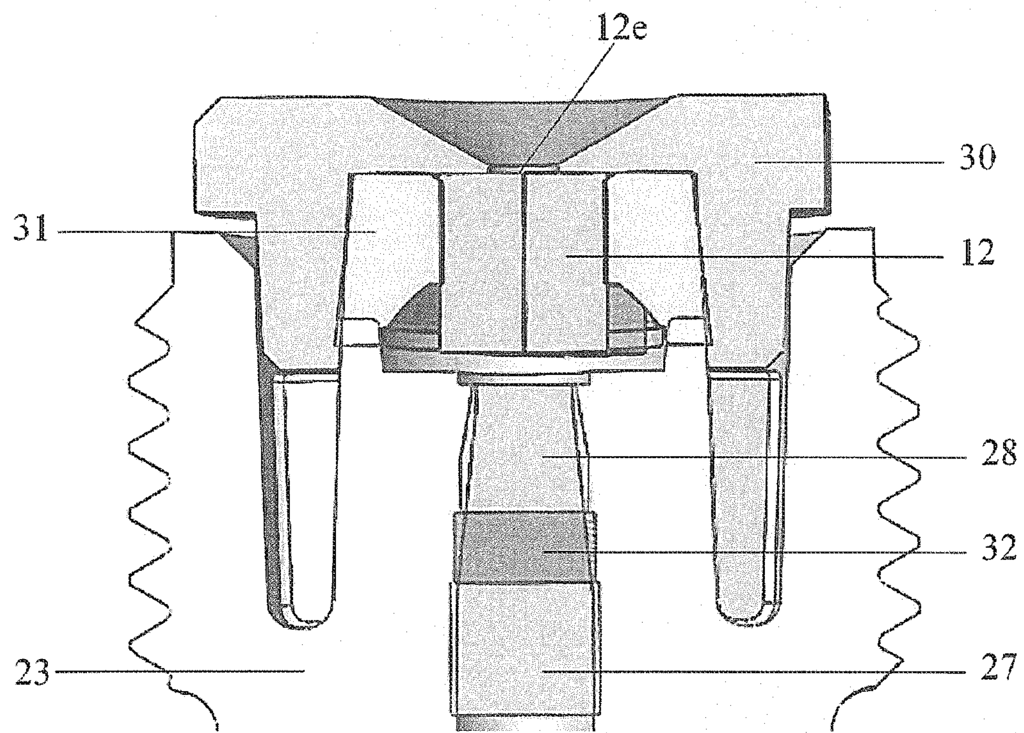
FIG. 6 is a schematic section through the nozzle assembly of the nebulizer with a pre-mounted filter system, according to an embodiment with an adsorption filter.
Figure 7:
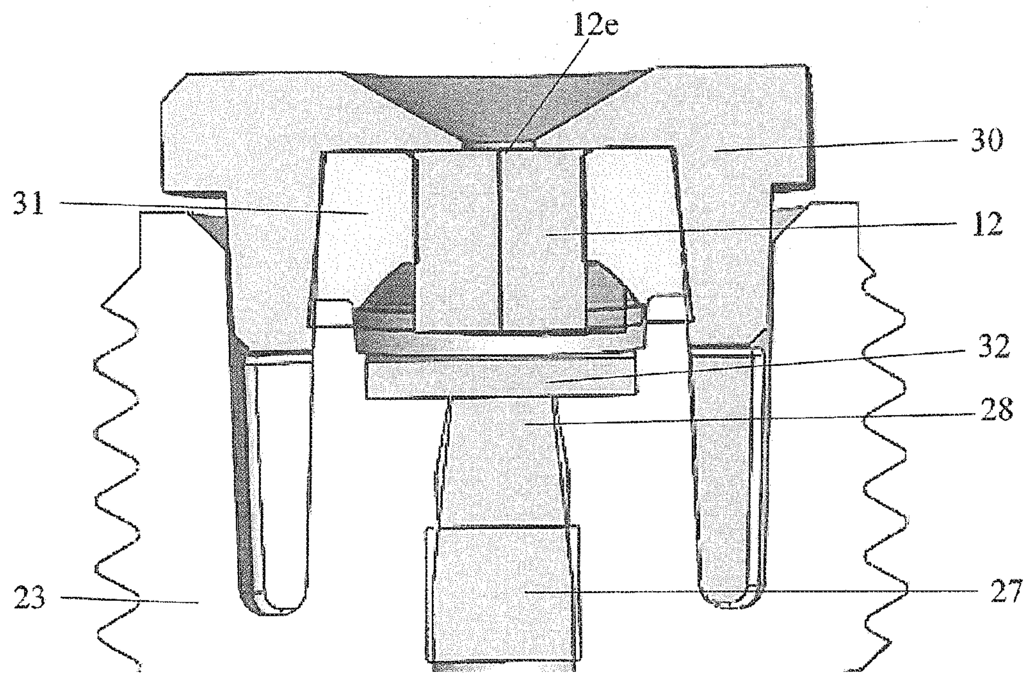
FIG. 7 is a schematic section through the nozzle assembly of the nebulizer with a pre-mounted filter system, according to another embodiment with an adsorption filter.
Figure 8:
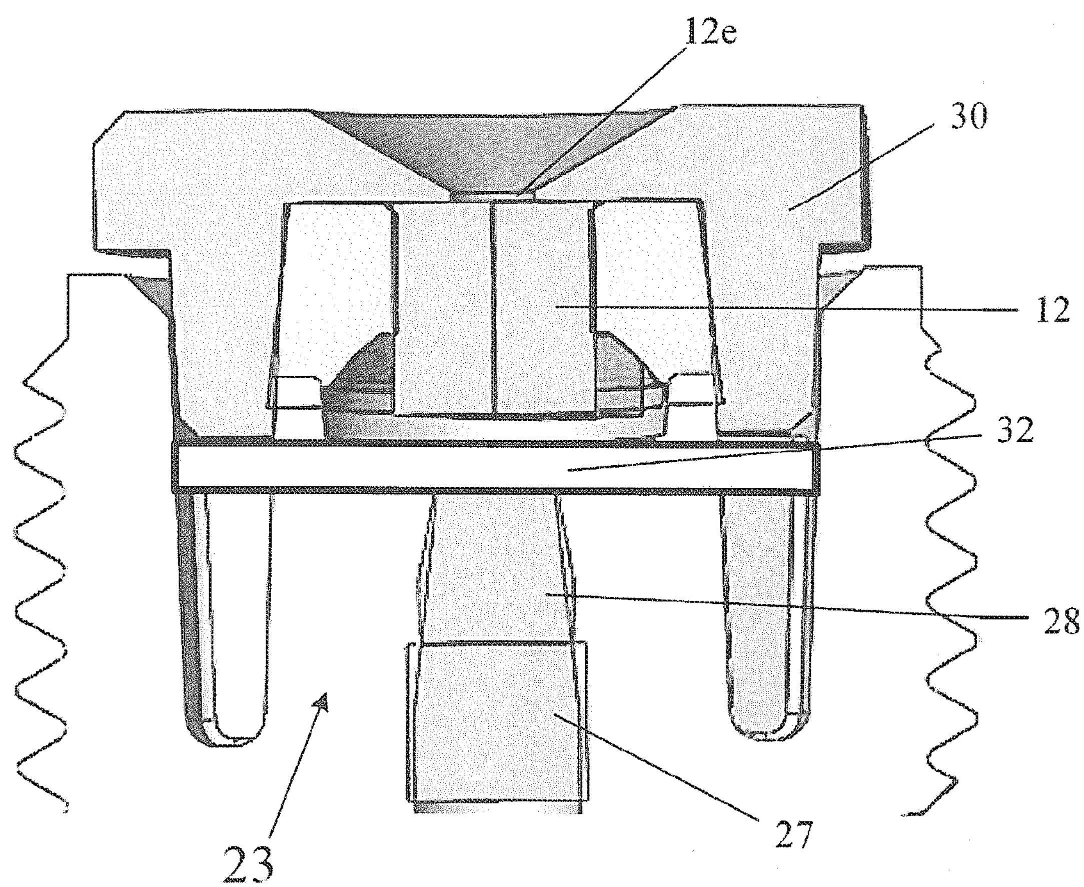
FIG. 8 is a schematic section through the nozzle assembly of the nebulizer with a pre-mounted filter system, according to yet another embodiment with an adsorption filter.

FIGS. 6 to 8 show, in an enlarged view, the nozzle assembly group (29) with the filter system arranged in front of it, in various embodiments, which, compared with the embodiment shown in FIG. 3, all contain a separate adsorption filter (32) as an additional filter to the pre-filter (27), fine filter (28) and very fine filter (12*f*). Besides the new aspects resulting from the adsorption filter (32), the aspects described with reference to FIG. 3 also apply in these embodiments as well. The adsorption filter (32) is arranged, as desired, between the pre-filter (27) and fine filter (28) (FIG. 6) or between the fine filter (28) and microstructured component (12) with very fine filter (12*f*) and nozzle (FIGS. 7 and 8).

In the embodiment according to FIG. 6, the adsorption filter (32) adjoins the pre-filter (27), viewed in the direction of flow. The adsorption filter (32) serves to separate off nanoparticles in the size range <<100 nanometers, which may accumulate at the outlets of the nozzle on the microstructured component (12). The adsorption filter (32) is made from a glass fiber functionalized using aluminium oxides, as a carrier fiber, and is frictionally secured between the pre-filter (27) and a fine filter (28)—preferably of titanium—for filtering particles up to about 3 to 5 μm in size.

The microstructured component (12) forming the nozzle is a glass/silicon composite in the embodiment shown. The microstructured component (12) is fixed to the nebulizer by means of a holder (30) with an associated seal (31). This microstructured component (12) contains not only the nozzle with the nozzle openings (12*e*) for producing microscopic liquid jets but also a very fine filter (12*f*) which is embodied as a zigzag-shaped flow filter according to FIG. 4 and serves to remove particles up to a size of about 2 μm from the liquid medical formulation in the flow path before the nozzle channels (12*d*) and/or the nozzle openings (12*e*). As a result of the connection of the microstructures of nozzle and very fine filter (12*f*) in a microstructured component (12), the very fine filter (12*f*) is arranged downstream of the fine filter (28) in the direction of flow. As shown in FIG. 6, the adsorption filter (32) may be enclosed between two filter systems in an interlockingly and/or frictionally connected manner. In the embodiment shown, it is pressed in between the pre-filter (27) and the fine filter (28) in the central part (23).

In alternative embodiments according to FIGS. 7 and 8, the fine filter (28) is arranged downstream of the pre-filter (27) and the adsorption filter (32) is located directly between the fine filter (28) and the very fine filter (12*f*). In the preferred embodiments shown in FIGS. 7 and 8, the adsorption filter (32) is embodied as a filter disc that is frictionally secured at its edge. Expediently, the edge of the filter disc is held either by a seal (31) of the microstructured component (12) that comprises the very fine filter (12*f*) and the nozzle, or by a holder (30) in the nozzle assembly (29) (FIG. 8), or by the microstructured component (12) itself (FIG. 7). Because of the diameter of the filter disc which is larger than that of the fine filter (28), and the fact that the fine filter (28) and filter disc are arranged one directly behind the other, the edge of the adsorption filter (32) is outside the flow path. Because the edge of the adsorption filter (32) is not located in the flow path, there is no danger that components of the adsorption filter (32) will be emitted through bypasses during use, as may often happen at the cut edge around the rim. The essential difference between the two installation situations shown in FIGS. 7 and 8 is the diameter of the adsorption filter (32) which is smaller when it is secured by the microstructured component (12) than when it is held by components that comprise the microstructured component (12), such as the holder (30) and the seal (31). With the usual dimensions of a microstructured component (12) of this kind, for the two scenarios, diameters of about 2 to 5 mm, preferably about 3 mm, are obtained for the adsorption filter when it is secured by the microstructured component (12) and about 3 to 10 mm, preferably about 6 mm when it is secured by the holder (30) and/or seal (31). In the embodiment according to FIG. 8, the adsorption filter (32) provided between the fine filter (28) and the very fine filter (12*f*) has a diameter such that it is clamped at its edges by the holder (30) of the microstructured component (12).

The idea of arranging filter elements of different types and with different actions one behind the other can be applied to numerous devices in which liquids are conveyed or transported. It is the case that the proposed nebulizer (1), in particular, operates purely mechanically. However, the filter system proposed here is not limited to use in purely mechanical devices for dispensing a liquid. It may also be used, for example, in systems in which the delivery of the liquid is actuated by propellant gas or by electric, hydraulic or other pumps. Terms such as "pressure generator" must therefore be interpreted broadly. In this sense the present invention may also be used across different sectors; even applications beyond the medical field are possible.

The nebulizer shown here is indeed used particularly for dispensing a liquid medical formulation as an inhalable aerosol and is suitable for delivering both aqueous and also preferably alcoholic, especially ethanolic medical formulations.

Preferred contents of the preferably liquid medical formulation are mentioned in particular in the specifications WO09/047173A2 and WO09/115200A1 which are hereby included in their entirety by way of references. In particular, the fluid described in these specifications may be aqueous or non-aqueous solutions, mixtures, formulations with and without solvents, such as ethanol or the like.

| List of reference numerals | |
|---|---|
| 1 | nebulizer |
| 2 | liquid |
| 3 | container |
| 5 | pressure generator |
| 6 | holder (for container) |
| 7 | drive spring |
| 8 | locking ring |
| 9 | hollow piston |
| 10 | non-return valve |
| 11 | pressure chamber |
| 12 | microstructured component |
| 12a | plate |
| 12b | plate |
| 12c | inflow region |
| 12d | nozzle channels |
| 12e | nozzle openings |
| 12f | very fine filter |
| 14 | aerosol |
| 16 | upper housing part |
| 17 | inner housing part |
| 18 | lower housing part |
| 19 | safety closure |
| 23 | central part |
| 24 | seal |
| 25 | support ring |
| 27 | pre-filter |
| 28 | fine filter |
| 29 | nozzle assembly |
| 30 | holder |
| 31 | seal |
| 32 | adsorption filter |
| 40 | button |
| 41 | counter |

The invention claimed is:

1. A device for administering a liquid medical formulation, comprising:

at least one nozzle opening (12*e*) for receiving the liquid medical formulation in a flow path through the device and expelling the liquid medical formulation from the device, a container (3) holding and sourcing the liquid medical formulation into the flow path, a very fine filter (12*f*) formed by a microstructured component (12) arranged upstream of the at least one nozzle opening (12*e*) in the flow path and operating to filter the liquid medical formulation prior to the at least one nozzle opening (12*e*), a fine filter (28) arranged upstream of the microstructured component (12) in the flow path of the liquid medical formulation and operating to filter the liquid medical formulation prior to the very fine filter (12*f*), a pre-filter (27) arranged upstream of the fine filter (28) in the flow path of the liquid medical formulation and operating to filter the liquid medical formulation prior to the fine filter (28), wherein:

the pre-filter (27) is of a relatively course filtering characteristics as compared with the fine filter (28) such that the pre-filter (27) prohibits particles of greater size that a first threshold from passing therethrough but permits particles of less than the first threshold to pass to the fine filter (28), the fine filter (28) is of a relatively fine filtering characteristic as compared with the pre-filter (27) and a relatively course filtering characteristic as compared with the microstructured component (12) such that the fine filter (28) prohibits particles of greater size that a second threshold from passing therethrough but permits particles of less than the second threshold to pass to the microstructured component (12), and the microstructured component (12) is of a relatively very fine filtering characteristic as compared with the fine filter (28) such that the microstructured component (12) prohibits particles of greater size that a third threshold from passing therethrough but permits particles of less than the third threshold to pass to the at least one nozzle opening (12*e*), wherein the pre-filter (27), the fine filter (28), and the very fine filter (12*f*) of the microstructured component (12) each have a different, respective pore size and are arranged so that the respective pore size decreases in the direction of flow.

2. The according to claim 1, characterized in that pre-filter (27), fine filter (28) and very fine filter (12*f*) consist of different materials.

3. The according to claim 1, characterized in that at least one of the pre-filter (27) and the fine filter (28) is made of sintered metal comprising metal particles that have been compressed into a fine-pored structure.

4. The according to claim 3, characterized in that the sintered metal is titanium.

5. The according to claim 3, characterized in that the pore sizes of the fine-pored structure are less than 5 microns.

6. The according to claim 1, characterized in that the pre-filter (27) is a plastics filter, and the microstructured component (12) is made of a glass/silicon composite.

7. The according to claim 1, characterized in that the fine filter (28) is a filter the mode of action of which is determined predominantly by adsorption effects and less by size exclusion, while particles from a liquid flowing through the fine filter are able to accumulate on the surface of the filter as a result of intermolecular interactions.

8. The according to claim 1, characterized in that an adsorption filter (32) is arranged in the flow path between pre-filter (27) and very fine filter (12*f*), the mode of action of the adsorption filter being characterized in that particles from a liquid flowing through the filter are able to accumulate on the surface of the filter as a result of intermolecular interactions.

9. The according to claim 8, characterized in that the adsorption filter (32) is embodied as a filter disc which is frictionally secured by its edge.

10. The according to claim 9, characterized in that the edge of the filter disc is held either by a component that seals off or fixes the microstructured component (12) or the nozzle in its installed position, or by the microstructured component (12) or the nozzle itself, or is clamped in position between the pre-filter (27) and fine filter (28).

11. The according to claim 8, characterized in that the adsorption filter (32) is arranged as an independent component either between the pre-filter (27) and the fine filter (28) or between the fine filter (28) and the very fine filter (12*f*).

12. The according to claim 8, characterized in that the adsorption filter (32) is made of glass, cellulose, carbon or polymer fibers.

13. The according to claim 8, characterized in that the adsorption filter (32) comprises a surface functionalized with aluminium oxide.

14. The according to claim 8, characterized in that the adsorption filter (32) has a surface functionalized with quaternary ammonium groups.

15. The according to claim 1, characterized in that pre-filter (27) and fine filter (28) have a circular-cylindrical or at least partially conical configuration.

16. The according to claim 1, characterized in that the liquid medical formulation that is to be administered contains a substance with a low vapor pressure or an alcoholic compound.

17. The according to claim 1, characterized in that the liquid medical formulation that is to be administered has a pH of between 3.5 and 9.

18. The according to claim 1, characterized in that the liquid medical formulation is delivered as an inhalable aerosol.

19. The according to claim 1, characterized in that the device contains a pressure chamber (11) and the filters are arranged between the pressure chamber (11) and the at least one nozzle opening (12*e*).

20. The according to claim 1, characterized in that the device comprises a central part (23) in which pre-filter (27) and fine filter (28) are arranged downstream of a pressure chamber (11) or a metering chamber.

21. The according to claim 20, characterized in that pre-filter (27) and fine filter (28) are held in the central part (23) without any additional components for securing them by a reduction in the internal cross-section formed by the central part itself (23), and/or by a press-fit.

22. A method of assembling a device according to claim 19, characterized in that fine filter (28) and pre-filter (27) are inserted into a central part (23) through what is to be the pressure chamber (11) and the insertion opening is closed off by the piston of a pressure generator (5) or by a connecting element formed as a hollow piston (9) for subsequently withdrawing liquid (2) from a container (3).

* * * * *